United States Patent [19]

Marangos et al.

[11] Patent Number: 5,187,162

[45] Date of Patent: Feb. 16, 1993

[54] METHODS OF TREATING NEURODEGENERATIVE CONDITIONS

[75] Inventors: Paul Marangos, Encinitas; Harry E. Gruber, San Diego, both of Calif.

[73] Assignee: Gensia Pharmaceuticals, San Diego, Calif.

[21] Appl. No.: 582,630

[22] Filed: Sep. 12, 1990

Related U.S. Application Data

[63] Continuation-in-part of Ser. No. 407,913, Sep. 15, 1989, abandoned.

[51] Int. Cl.$^5$ ............................................. A61K 31/70
[52] U.S. Cl. ......................................... 514/46; 514/43; 514/45; 514/44; 514/47; 514/48; 514/821; 536/26.7; 536/27.6
[58] Field of Search ......................... 514/46, 43, 45, 44, 514/47, 48, 821; 536/23, 24, 26, 27

[56] References Cited

PUBLICATIONS

Sonsalla, et al. "Role for Excitatory Amino Acids in Methamphetamine-Induced Nigrostrial Dopaminergic Toxicity" Science 243: 398–400 (1989).

Snyder, S. H. "Adenosine as a Neuromodulator" Ann. Rev. Neural Sci. 8: 103–124 (1985).

Marangos, et al. "Basic and Clinical Aspects of Adenosinergic Neuromodulation" NeuroSci & Biobehav. Rev. 9: 421–430 (1985).

Dunwiddie, T. V. "The Physiological Role of Adenosine in the Central Nervous System" Int. Rev. Neurobiol., 27: 63–130 (1985).

Phillis, et al. "A Potent Depressant Action of Adenine Derivatives on Cerebral Cortical Neurones" Europ. J. Pharmacol. 30: 125–129 (1975).

Dunwiddie, et al. "Sedative and Anticonvulsant Effects of Adenosine Analogs in Mouse and Rat" J. Pharmacol. and Exptl. Therapeut. 220: 70–76 (1982).

Radulovacki, et al. "Adenosine Analogs and Sleep in Rats" J. Pharmacol. Exptl. Therapeut. 228: 268–274 (1981).

Lee et al. "The Anticonvulsive Action of Adenosine: A Postsynaptic, Dendritic Action by a Possible Endogenous Anticonvulsant" Brain Res. 21: 160–164 (84).

Paterson, et al. "Transport of Nucleosides" Annals of the New York Academy of Sciences, vol. 255, p. 402 (1975).

Deckert, et al. "Adenosine Uptake Site Heterogeneity in the Mammalian CNS? Uptake Inhibitors as Probes and Potential Neuropharmaceuticals" Life Sci. vol. 42 pp. 1331–1345.

Londos, et al. "Adenosine Receptors and Adenylate Cyclase Interactions" Regulatory Function of Adenosine, pp. 17–32.

Carson et al. "Effect of Adenosine Deaminase Inhibition upon Human Lymphocyte Blastogenesis" Journal of Clinical Investigation V. 57, p. 274 (76).

Church et al. "Phencyclidine/Sigma Receptor Agonists: Anticonvulsant Properties Due To N-Methylaspartate (NMA) Antagonism?" Excitatory Amino Acid Transmission pp. 115–118 (1987).

Daval et al. "Protective Effect of Cyclohexyladenosine on Adenosine $A_1$-receptors, Guanine Nucleotide and Forskolin Binding Sites Following Transient Brain Ischemia: A Quantitative Autoradiographic Study" Brain Res. 491: 212–226 (1989).

(List continued on next page.)

Primary Examiner—Ronald W. Griffin
Attorney, Agent, or Firm—Lyon & Lyon

[57] ABSTRACT

Methods of preventing neural tissue damage caused by excitotoxicity due to increased release of excitatory amino acids by increasing extracellular concentrations of adenosine in and around the neural tissue are provided. These methods are especially useful in treating neurodegenerative diseases such as Parkinson's Disease, Alzheimer's Disease, Amyotrophic Lateral Sclerosis or Huntington's Disease.

26 Claims, 4 Drawing Sheets

OTHER PUBLICATIONS

Marangos, "Adenosinergic Approaches to Stroke Therapeutics" Med. Hypotheses 32: 45–49 (1990).

Helgason, "Blood Glucose and Stroke" Stroke, 19(8): 1049–1053 (1988).

LeMay et al. "Insulin Administration Protects Neurologic Function in Cerebral Ischemia in Rats" Stroke, 19(11): 1411–1419 (1988).

Markey et al. "The Pharmacology of the Parkinsonian Syndrome Producing Neurotoxin MPTP (1-Methyl-4-Phenyl-1,2,3,6-Tetrahydropyridine and Structurally Related Compounds" Medicinal Research Rev. 6(4): 389–429 (1986).

Reinhard et al. "A Rapid and Sensitive Assay for Tyrosine-3-Monooxygenase Based upon The Release of $^3H_2O$ and Adsorption of 3H-Tyrosine by Charcoal" Life Sci., 39: 2185–2189 (1986).

Dragunow, et al. "Is Adenosine an Endogenous Anticonvulsant" Epilepsia, 26(5):480–487 (1985).

Fox & Kelly "The Role of Adenosine and 2'-Deoxyadenosine in Mammalian Cells" Ann. Rev. Biochem. 47:655–86 (1978).

Gruber, et al. "Levels of dATP in ADA-inhibited Human Peripheral Blood B and T Lymphocytes Cultured in Deoxyadenosine[a]" Annals of New York Acad. Sci. pp. 315–318.

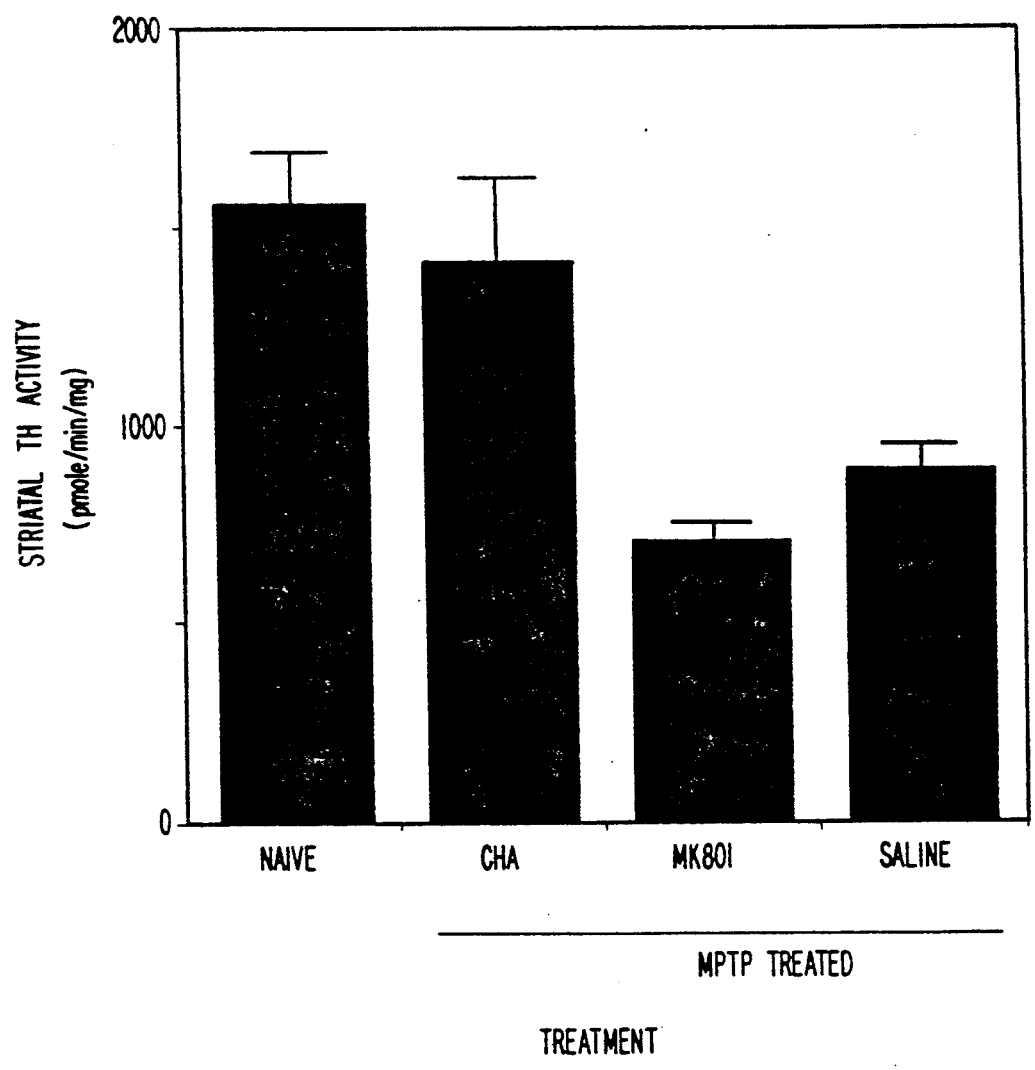

METHODS OF TREATING NEURODEGENERATIVE CONDITIONS

CROSS-REFERENCE TO THE APPLICATION

This case is a CIP of U.S. application Ser. No. 407,913 filed Sept. 15, 1989, now abandoned.

BACKGROUND OF THE INVENTION

The present invention is directed to methods of treating neurodegenerative conditions by increasing extracellular concentrations of adenosine.

The etiology of major neurodegenerative diseases is not understood. Such diseases, which include Parkinson's Disease, Huntington's Disease, Amyotrophic Lateral Sclerosis (ALS or Lou Gehrig's Disease) and Alzheimer's Disease, have proved difficult to treat; few if any therapies have proved effective in slowing or arresting the degenerative process.

Parkinson's Disease is a prevalent neurodegenerative disease which generally affects older people. As noted above, its specific etiology is not well understood; however, a Parkinson-like syndrome can result from exposure to certain chemical substances. Two such substances, methamphetamine and 1-methyl-4-phenyl-1,2,3,6-tetrahydropyridine (MPTP), have been used as models for studying Parkinson's Disease.

Parkinson's Disease is characterized by lesions in the brain, particularly affecting the striatum and results in dopamine depletion, particularly in the striatum (nuclei of the basal ganglia, especially substantia nigra, putamen and caudate nucleus). Attempts to alleviate the dopamine depletion in individuals affected with Parkinson's Disease led to the use of L-dopa, a precursor to dopamine which is better able to cross the blood-brain barrier, as a therapeutic agent to alleviate the symptoms of Parkinson's Disease. In order to better target the global effects of L-dopa, it is often given with carbidopa, a peripheral decarboxylase inhibitor which decreases the metabolism of L-dopa in the peripheral tissues.

The systemic administration of either methamphetamine or MPTP to experimental animals has been found to produce degenerative changes in nigrostriatal dopaminergic neurons or their axon terminals Both methamphetamine and MPTP result in decreases in striatal dopamine (DA) and in decreased tyrosine hydroxylase (TH) activity, as well as histochemical indications of nerve terminal degeneration within the neostriatum. It has been postulated that some of those neurodegenerative effects may be associated with overactivity of excitatory amino acid (EAA) neurotransmission. Treatment with noncompetitive blockers of one of the EAA receptors, the N-methyl-D-aspartate (NMDA) receptor has been shown to partially antagonize NMDA-mediated decrements in DA content and TH activity produced by administration of methamphetamine or MPTP. It was postulated that those findings implicated EAA's in neurodegenerative conditions such as Parkinson's Disease. (See, Sonsalla, P. K., et al. "Role for Excitatory Amino Acids in Methamphetamine-Induced Nigrostrial Dopaminergic Toxicity", Science 243: 398–400 (1989)).

Due to their mimicry of effects of Parkinson's Disease, treatment of animals with methamphetamine or MPTP has been used to generate models for Parkinson's Disease. These animal models have been used to evaluate the efficacy of various therapies against Parkinsons's Disease Administration of MPTP to animals provides a useful Parkinsonian model. The end result of MPTP administration is the destruction of the striatum in the brain, an area in the neocortex limbic system in the subcortical area in the center of the brain, an area compromised in Parkinson's Disease. The neurotransmitter dopamine is concentrated in the striatum Parkinson's Disease is characterized by lesions in that area of the brain and by depleted dopamine levels. In some species (primates) the striatal degeneration has been reported to be accompanied by behavioral symptoms that mimic Parkinson's symptoms in humans.

Methamphetamine also compromises the striatum, but is somewhat less selective than MPTP and may induce strial degeneration by a different mechanism than MPTP.

Adenosine, 9-$\beta$-D-ribofuranosyladenine (the nucleoside of the purine adenine), belongs to the class of biochemicals termed purine nucleosides and is a key biochemical cell regulatory molecule, as described by Fox and Kelly in the *Annual Reviews of Biochemistry*, Vol 47, p. 635, 1978.

Adenosine interacts with a wide variety of cell types and is responsible for a myriad of biological effects. Adenosine serves a major role in brain as an inhibitory neuromodulator (see Snyder, S. H., *Ann. Rev. Neural Sci.* 8: 103-124 1985, Marangos, et al., *NeuroSci and Biobehav Rev.* 9:421-430 (1985), Dunwiddie, *Int. Rev. Neurobiol.*, 27:63-130 (1985)). This action is mediated by ectocellular receptors (Londos et al., *Regulatory Functions of Adenosine*, pp. 17-32 (Berne et al., ed.) (1983)). Among the documented actions of adenosine on nervous tissue are the inhibition of neural firing (Phillis et al., *Europ. J. Pharmacol.*, 30:125-129 (1975)) and of calcium dependent neurotransmitter release (Dunwiddie, 1985). Behaviorally, adenosine and its metabolically stable analogs have profound anticonvulsant and sedative effects (Dunwiddie et al., *J. Pharmacol. and Exptl. Therapeut.*, 220:70-76 (1982); Radulovacki et al., *J. Pharmacol. Exptl. Thera.*, 228:268-274 (1981)) that are effectively reversed by specific adenosine receptor antagonists. In fact, adenosine has been proposed to serve as a natural anticonvulsant, and agents that alter its extracellular levels are modulators of seizure activity (Dragunow et al., *Epilepsia* 26:480-487 (1985); Lee et al., *Brain Res.*, 21:1650-164 (1984)). In addition, adenosine is a potent vasodilator, an inhibitor of immune cell function, an inhibitor of granulocyte oxygen free radical production, an antiarrhythmic, and an inhibitory neuromodulator Considering its broad spectrum of biological activity, considerable effort has been aimed at establishing practical therapeutic uses for adenosine and its analogs.

Since adenosine is thought to act at the level of the cell plasma membrane by binding to receptors anchored in the membrane, past work has included attempts to increase extra-cellular concentrations of adenosine by administering it into the blood stream. Unfortunately, because adenosine is toxic at concentrations that have to be administered to a patient to maintain an efficacious extracellular therapeutic concentrations, the administration of adenosine alone is of limited therapeutic use. Further, adenosine receptors are subject to negative feedback control following exposure to adenosine, including down-regulation of the receptors.

Other ways of achieving the effect of a high local extracellular concentration of adenosine exist and have also been studied. They include: a) interference with the uptake of adenosine with reagents that specifically block adenosine transport, as described by Paterson et al., in the *Annals of the New York Academy of Sciences*, Vol. 255, p. 402 (1975); and Deckert et al., in *Life Sciences*, Vol. 42, page 1331 to 1345; b) prevention of the degradation of adenosine, as described by Carson and Seegmiller in *The Journal of Clinical Investigation*, Vol. 57, p. 274 (1976); and c) the use of analogs of adenosine selectively to bind to adenosine receptors.

Compounds which selectively increase extracellular adenosine would also be useful in the prophylactic protection of cells in the hippocampus implicated in memory. The hippocampus has more adenosine and glutamate receptors than any other area of the brain. Accordingly, as described below, it is most sensitive to stroke or any condition of low blood flow to the brain. Some recent studies suggest that Alzheimer's disease may result from chronic subclinical cerebral ischemia. Accordingly, compounds which selectively increase extracellular adenosine levels may be used for the treatment and/or prevention of both overt stroke and Alzheimer's disease.

It is now established that relatively short periods of brain ischemia (on the order of 2 to 8 minutes) set into motion a series of events that lead to an eventual death of selected neuronal populations in brain. This process is called delayed excitotoxicity and it is caused by the ischemia-induced enhancement of the release of the excitatory amino acid neurotransmitters, including glutamate and aspartate. Within a period of hours to days post-stroke, some neurons in brain are overstimulated by EAA's to the point of metabolic exhaustion and death. Because over-released glutamate appears to be the major factor involved in post-stroke cell damage, the blockade of glutamate receptors in brain could be beneficial in stroke therapy. In animals, glutamate receptor blockers have been shown to be effective in alleviating or preventing stroke-associated neural damage. These receptor blockers have, however, been shown to lack specificity and produce many undesirable side effects. Church, et al., "Excitatory Amino Acid Transmission," pp. 115-118 (Alan R. Liss, Inc. 1987).

Adenosine has been shown to be a potent inhibitor of glutamate release in brain. The CA-I region of brain is selectively sensitive to post-stroke destruction. In studies where observations were made at one, three and six days poststroke, the CA-I area in the hippocampus was shown to be progressively destroyed over time. However, where cyclohexyladenosine ("CHA"), a global adenosine agonist, was given shortly after the stroke, the CA-1 area was markedly protected. (Daval et al., *Brain Res.*, 491:212-226 (1989) and Marangos, Med. Hypothesis 32:45-49 (1990)). That beneficial effect was also seen in the survival rate of the animals. Because of its global effect, however, CHA has non-specific side effects. For example it undersirably will lower blood pressure, slow the heart and markedly raise blood glucose.

Hyperglycemia has been reported to be associated with a poor prognosis for stroke (Helgason, *Stroke* 19(8) :1049-1053 (1988)). In addition, mild hypoglycemia induced by insulin treatment has been shown to improve survival and morbidity from experimentally induced infarct (LeMay et al., Stroke 19(11):1411-1419 (1988)). AICA riboside and the prodrugs of the present invention could protect against ischemic injury to the central nervous system (CNS) by their ability to lower blood glucose.

Another area of medical importance is the treatment of neurological diseases or conditions arising from elevated levels of homocysteine (e.g., vitamin B12 deficiencies). The AICA riboside prodrugs may be used for such purposes as well.

During seizures, certain neural cells fire abnormally. ATP catabolism is greatly accelerated in the abnormally firing cells leading to increased adenosine production. Adenosine has marked anticonvulsant effects and, thus, has been termed the brain's natural anticonvulsant. It appears to play a major role in the brain as an inhibitory neuromodulator; this action of adenosine is apparently mediated by certain ectocellular receptors. Adenosine has both post-synaptic and pre-synaptic effects. Among the documented effects of adenosine on nervous tissue are the inhibition of neural firing and of calcium dependent neurotransmitter release. Behaviorally, adenosine and its metabolically stable analogs have profound anticonvulsant and sedative effects.

As stated above, adenosine has been proposed to serve as a natural anticonvulsant with agents that alter its extra-cellular concentration acting as a modulator of seizure activity Besides acting as a neuromodulator, adenosine is a potent vasodilator, an inhibitor of granulocyte oxygen free radical production, an antiarrhythmic. In fact, because of the many actions of adenosine, it has been called a "retaliatory molecule" released to protect cells against certain pathologic assaults.

Unfortunately, adenosine is toxic at concentrations that have to be administered systemically to a patient to maintain an efficacious extracellular therapeutic concentration at the target organ, and the administration of adenosine alone so far has been of limited therapeutic use. Likewise, since most cells in the body carry receptors for adenosine, the use of techniques that increase adenosine concentrations generally throughout the body can cause unwanted, dramatic changes in normal cellular physiology.

SUMMARY OF THE INVENTION

The present invention is directed to methods of preventing or decreasing neural tissue damage associated with neurodegenerative diseases in an affected individual which comprises increasing the extracellular concentrations of adenosine in said neural tissue In one aspect of the present invention, the extracellular adenosine concentrations are increased by administering to the affected individual a therapeutically effective amount of an agent which increases extracellular adenosine. Suitable agents for increasing extracellular adenosine concentrations include adenosine regulating agents (e.g. inhibitors of adenosine catabolism and enhancers of adenosine production), inhibitors of adenosine transport, and adenosine agonists.

One particularly preferred group of agents which act as adenosine regulating agents comprise AICA riboside or AICA ribo-side prodrugs which comprise a modified AICA riboside having an AICA ribosyl moiety and at least one hydrocarbyloxycarbonyl or hydrocarbylcarbonyl moiety per equivalent weight of AICA ribosyl moiety.

In another aspect, the present invention is directed to preventing neural tissue damage caused by increased release of excitatory amino acids (EAA) by increasing extracellular concentrations of adenosine.

The adenosine regulating agents, including AICA riboside and its prodrugs, described herein not only show the beneficial adenosine regulating/EAA inhibiting properties, but also are both site and event specific, avoiding the unwanted global action of known adenosine agonists.

In an additional aspect, the present invention is directed to the treatment of Parkinson's Disease in an affected individual and related neurodegenerative diseases by increasing the extracellular concentration of adenosine in the brain of that individual. Such diseases include Alzeheimer's Disease, Amyotropic Lateral Sclerosis (ALS) and Huntington's Disease.

BRIEF DESCRIPTION OF THE DRAWINGS

FIG. 4 depicts a comparison of the effect of CHA and MK-801 on MPTP-induced decrease in tyrosine hydroxylase activity.

DETAILED DESCRIPTION OF THE INVENTION

Figure 1:
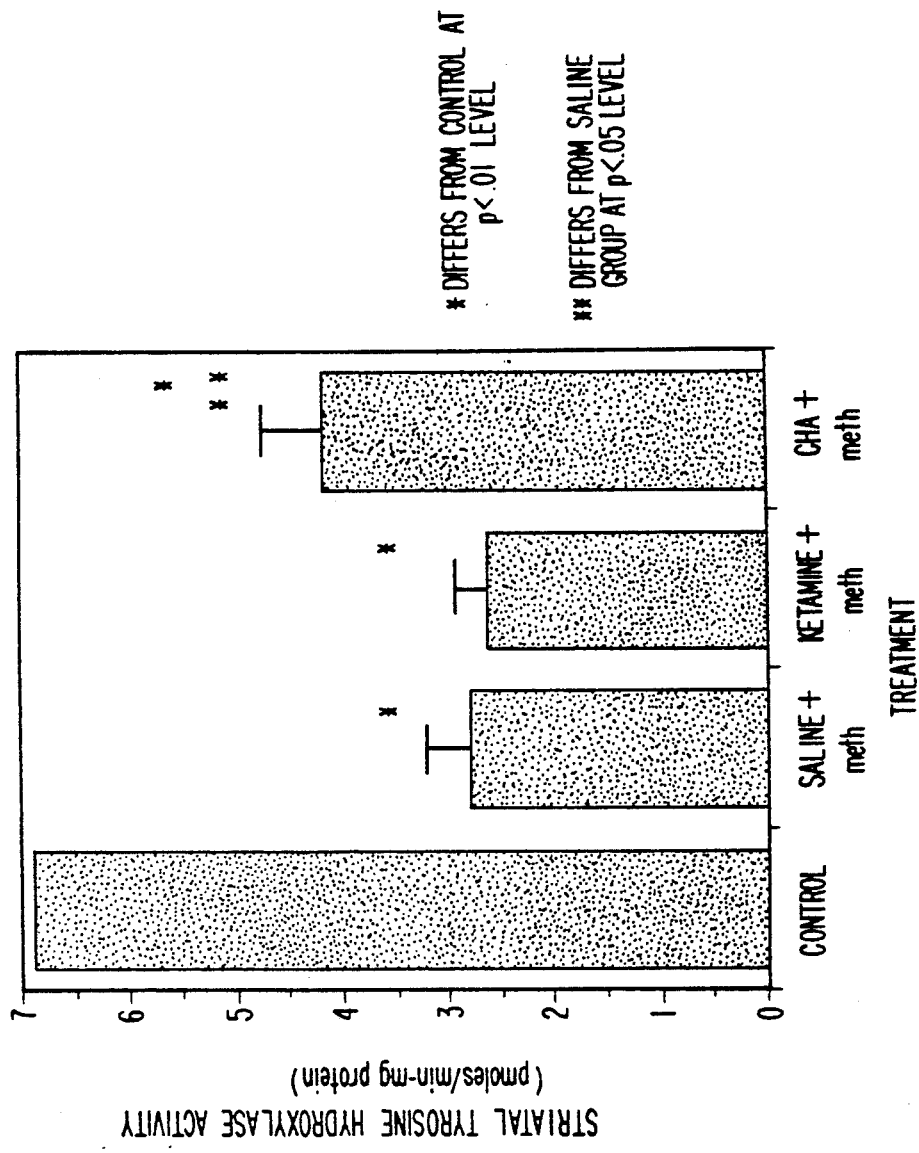
FIG. 1 depicts the effect of Ketamine and CHA on the development of Methamphetamine-induced Parkinson Syndrome

The methods of the present invention are directed to preventing or decreasing neural tissue damage by increasing the extracellular concentrations of adenosine or adenosine agonists in the neural tissue. One mechanism proposed for this protective effort involves inhibition of excitatory amino acid (EAA) induced neural toxicity. Excitotoxicity has been implicated in the methamphetamine animal model of Parkinson's Disease (Sonsalla et al., Science 243:398–400 (1989)). According to the methamphetamine model, a neurodegenerative mechanism involves the release of newly synthesized dopamine oxidation products which exhibit neurotoxicity. Another neurodegenerative disease model involves methylphenyltetrahydropyridine (MPTP) which is thought to cause damage by glial conversion of MPTP to 1-methyl-4-phenylpyridinium ion ("MPP.") and which is then thought to be selectively taken up by dopaminergic neurons and which produces superoxide in mitochondria by redox cycling using neuromelanin as an electron source. (See, Markey, et al., Medicinal Research Reviews 6(4):389–429 (1986)).

The methods of the present invention have shown efficacy in protecting against neurodegenerative effects in both the methamphetamine and MPTP models.

Preferred Adenosineroic Compounds

One aspect of the present invention is directed to the use of agents which enhance extracellular adenosine levels to protect against neurodegenerative damage. As noted, these agents include adenosine regulating agents such as AICA riboside and, analogs and prodrugs thereof.

Agents which enhance extracellular adenosine concentrations include inhibitors of adenosine transport or adenosine regulating agents, e.g. inhibitors of adenosine catabolism or enhancers of adenosine production.

Agents that can inhibit the cellular transport of adenosine include those that do so specifically, and are essentially competitive inhibitors of adenosine uptake, and others that inhibit nonspecifically. P-nitrobenzylthioinosine and dipyradamole appear to be competitive inhibitors, while a variety of other chemicals, including colchicine, phenethyalcohol and papaverine inhibit uptake nonspecifically.

Alternatively, extracellular concentrations of adenosine can be increased by the use of chemicals that inhibit enzymatic degradation of adenosine. One group includes inhibitors of adenosine deaminase, an enzyme which participates in the conversion of adenosine to inosine. Inhibitors of adenosine deaminase activity include coformycin, 2'-deoxycoformycin, and erythro-9-(2-hydroxy-3-nonyl) adenine hydrochloride.

Adenosine receptor agonists and antagonists include adenosine analogs which have structural modifications in the purine ring, alterations in substituent groups attached to the purine ring, and modifications or alterations in the site of attachment of the carbohydrate moiety.

Although inhibitors of adenosine transport, inhibitors of adenosine deaminase and adenosine agonists provide advantages in increasing extracellular adenosine over the use of adenosine alone, they may exhibit disadvantages which include adverse side effects, primarily due to the fact that they must be administered in doses that are toxic, and have nonselective effects on most cell types. Since most cells in the body have functional receptors for adenosine, techniques that increase adenosine concentrations generally throughout the body can cause unwanted, dramatic changes in normal cellular physiology. (See, *Purine metabolism in Man*, (eds. De Baryn, Simmonds and Muller), Plenum Press, New York (1984)). In addition, adenosine deaminase inhibitors prevent the degradation of deoxyadenosine which is a potent immunotoxin. (see Gruber et al. Ann. New York Acad. Sci. 451:315–318 (1985)).

Accordingly, adenosinergic agents which selectively increase extracellular adenosine levels in the areas of the brain affected by a neurodegenerative condition, such as Parkinson's Disease, are preferred. Thus, a preferred aspect of the methods of the present invention is directed to the use of adenosine regulating agents which selectively enhance extracellular adenosine concentration in neural tissue to protect against neurodegenerative damage.

Methods for enhancing extracellular adenosine concentrations utilize the administration of compounds which are believed to alter one or more of the biochemical pathways of adenosine metabolism (e.g., adenosine kinase, AMP deaminase, AMP nucleotidase), so that the net result is an enhanced extracellular concentration of adenosine. This may result from one or more processes, including enhanced intracellular production and/or decreased catabolism of adenosine). Examples of compounds useful in the methods of the present invention include compounds broadly classified as purine nucleosides and related analogs, such as AICA riboside, AICA ribotide, 1-β-D-ribofuranosyl-1B-1,2,4-triazole-3-carboxamide (ribavirin), ribavirin monophosphate, and various pro-forms of the above compounds. The compounds can be taken up by cells and, if necessary, are believed to be converted to their monophosphate and, to a lesser extent, their diphosphate and triphosphate forms. Also included are (1) agents that can enhance endogenous synthesis of AICA riboside or metabolites, such as purine intermediary metabolites or compounds that can form these metabolites, e.g., succinylaminoimidazole carboxamide (SAICA) riboside, (2) agents that cause a buildup of AICA-riboside or its metabolites, including methotrexate, and (3) agents that cause bacterial flora to increase AICA riboside production, such as sulfonamides. These compounds can be administered to a patient either prophylactically, in some cases, and/or in direct response to a bodily condition in others. Purine nucleosides or analogs that enhance the extracellular concentration of adenosine and/or adenosine analogs may be administered to a living system over the concentration range of 0.05 millimolar to 0.5 millimolar and, for AICA riboside typically, are administered in concentrations up to 0.5 millimolar.

Certain purine prodrugs and analogs which exhibit and, in some cases improve upon, the positive biological effects of AICA riboside and other adenosine regulating compounds without the negative effects of adenosine are disclosed in the commonly assigned pending patent application "AICA Riboside Prodrugs," U.S. Pat. No. 301, 222, filed Jan. 24, 1989, now U.S. Pat. No. 5,082,829, the commonly assigned patent application "Method and Compounds for AICA Riboside Delivery and for Lowering Blood Glucose" U.S. Pat. No. 408,107 filed Sept. 15, 1989, and "Methods and Compounds for AICA Riboside Delivery and for Lowering Blood Glucose, U.S. Pat. No. 466,979, filed Jan. 18, 1990, the disclosures of which are incorporated herein by reference. The compounds therein defined may be used as prodrugs. The novel compounds typically exhibit one or more of the following improvements over AICA riboside: 1) more potent adenosine regulating effects; 2) increased half-lives; 3) increased brain penetration; 4) increased oral bioavailability; 5) increased myocardial targeting; 6) in some cases synergism with AICA riboside itself The AICA riboside prodrugs may be used in methods of the present invention.

Adenosine or inosine are generated from adenosine triphosphate in the course of rapid cellular energy utilization, such as during seizure activity, arrhythmias, or a condition resulting in decreased blood flow (ischemia), such as a stroke, heart attack, or angina. Normally, during such an event, the production of inosine is greater than that of adenosine. In the area of low flow during coronary occlusion, for example, the ratio of inosine to adenosine is approximately 100 to 1. A certain percentage of inosine and adenosine subsequently exit the cell and are present in the immediate extracellular environment. These adenosine regulating agents are useful in the methods described herein and have been shown to enhance the extracellular concentration of adenosine, and the production of inosine has been shown to be decreased in some settings. Adenosine levels are not altered significantly throughout the patient because alterations in adenosine production only occur in areas of, and at the time of, net ATP use and because adenosine is rapidly degraded. Thus, the use of these adenosine regulating agents according to the methods of the present invention will cause a localized increased concentration of extracellular adenosine instead of a systemic or generalized adenosine enhancement.

Because the purine nucleoside analog AICA riboside can be metabolized to uric acid, this agent may be used with allopurinol or other drugs that prevent uric acid synthesis, or with a uricosuric agent such as probenecid. Certain agents, such as methotrexate and ribavirin, whose metabolites inhibit AICA riboside transformylase, may cause an elevation of endogenously synthesized AICA ribotide and create effects similar to administering the purine nucleoside. Concomitant administration of AICA riboside or AICA riboside with an inhibitor of AICA riboside transformylase should have at least additive effects. In addition, any one of the de novo purine nucleotide synthesis intermediates (after the first committed step for purine synthesis) or their nucleosides or bases can be assumed to be rapidly converted to AICA riboside. An example is SAICA riboside or its nucleotide or base.

Upon contact with cells, it is believed that the adenosine regulating purine nucleosides and analogs useful in the methods of the present invention enter the cell where, if necessary, they may be phosphorylated by adenosine kinase or, in the case of administration of base, they may be converted to a nucleotide by a phosphoribosyl transferase enzyme to yield a purine nucleotide monophosphate, and eventually also the nucleoside diphosphate or triphosphate. The diphosphate or triphosphate form may comprise a pool for breakdown to the monophosphate form.

In one aspect of the present invention, preferred AICA riboside prodrug compounds are used which include those having the following formula:

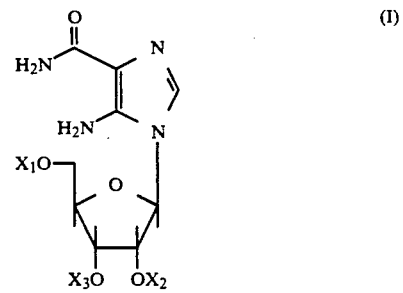

wherein $X_1$, $X_2$, and $X_3$ are independently (a) hydrogen, (b)

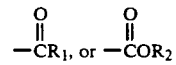

wherein $R_1$ is independently hydrocarbyl preferably of from 1 to about 24 carbon atoms, or independently mono- or di-hydrocarbylamino and $R_2$ is independently hydrocarbyl, preferably 1 to 24 carbon atoms, or (c) two of $X_1$, $X_2$ and $X_3$ taken together form a cyclic carbonate group, provided that at least one of $X_1$, $X_2$ and $X_3$ is not hydrogen. Preferred $R_1$ and $R_2$ groups include lower alkyl groups. One preferred class of lower alkyl groups are those having at least one secondary or tertiary carbon atom. Another preferred class of lower alkyl groups are those having up to about 6 carbon atoms. Hydrocarbyl groups having more than 24 carbon atoms may be used.

Preferred compounds include those having one or two ester groups. Especially preferred are compounds having an ester group at either the 3'- or 5'- position or both positions of the ribosyl ring.

Since for many indications, it would be advantageous and preferred to administer these prodrugs orally, those prodrugs which exhibit enhanced oral bioavailability would offer a therapeutic advantage. Accordingly, prodrugs where one or more of $X_1$, $X_2$ and $X_3$ comprises a short chain hydrocarbylcarbonyl group are preferred. In view of their enhanced bioavailability when given orally in either a liquid or solid (e.g., capsule) form, particularly preferred are those prodrugs where $X^1$ is isobutyryl or pivaloyl and $X_2$ and $X_3$ are both hydrogen, and where $X_1$, $X_2$ and $X_3$ are both acetyl. Also preferred are those prodrugs where $X_1$ is n-butyryl and $X_2$ and $X_3$ are both hydrogen, and where $X_1$ and $X_3$ are both acetyl and $X_2$ is hydrogen. Especially preferred are certain prodrug compounds which have been isolated in an advantageous crystalline form, in particular 2',3',5'-triacetyl AICA riboside 3',5'-diacetyl AICA riboside and 3'-neopentoxycarbonyl. Moreover, in the acetyl-substituted prodrug compounds, the leaving groups comprise acetate which is advantageously relatively pharmacologically silent.

Preparation of AICA Riboside Prodrug Compounds

The AICA riboside prodrug compounds may be conveniently prepared according to the following reaction scheme:

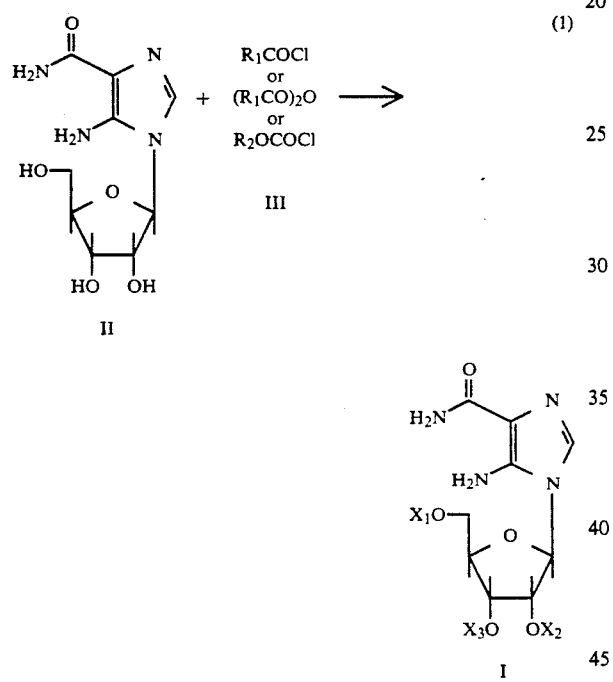

wherein $X_1$, $X_2$, $X_3$, $R_1$, and $R_2$ are as defined in conjunction with formula (I).

Reaction (1) is carried out by combining II, AICA riboside, and III, the appropriate acid chloride, acid anhydride or chloroformate, in solvent. The acid chloride may be conveniently prepared by conventional procedures such as reaction of the corresponding acid with thionyl chloride. Some acid chlorides and acid anhydrides are commercially available. Many chloroformates are commercially available; also, the chloroformates may be conveniently prepared by conventional procedures known to those skilled in the art by the reaction of phosgene with the appropriate alcohol. Reaction (1) is conducted at a temperature of from about $-10°$ C. to about $5°$ C., preferably from about $-5°$ C. to about $0°$ C and is generally complete within about 2 to about 4 hours. For ease of handling, the reaction is carried out in solvent. Suitable solvents include dimethylformamide (DMF), pyridine, methylene chloride and the like. For convenience, the reaction is carried out at ambient pressure. The reaction product(s) are isolated by conventional procedures as column chromatography, crystallization and the like. As may be appreciated, the reaction may result in a mixture of products, mono, di, and tri-esters at the 2'-, 3'- and/or 5'- positions of the ribosyl moiety. The product esters may be separated by conventional procedures such as thin layer chromatography (TLC), high pressure liquid chromatography (HPLC), column chromatography, crystallization, and the like which are well known to those skilled in the art.

The 5'-monoesters may be conveniently prepared according to the following reaction scheme to give an intermediate blocked at the 2' and 3' positions:

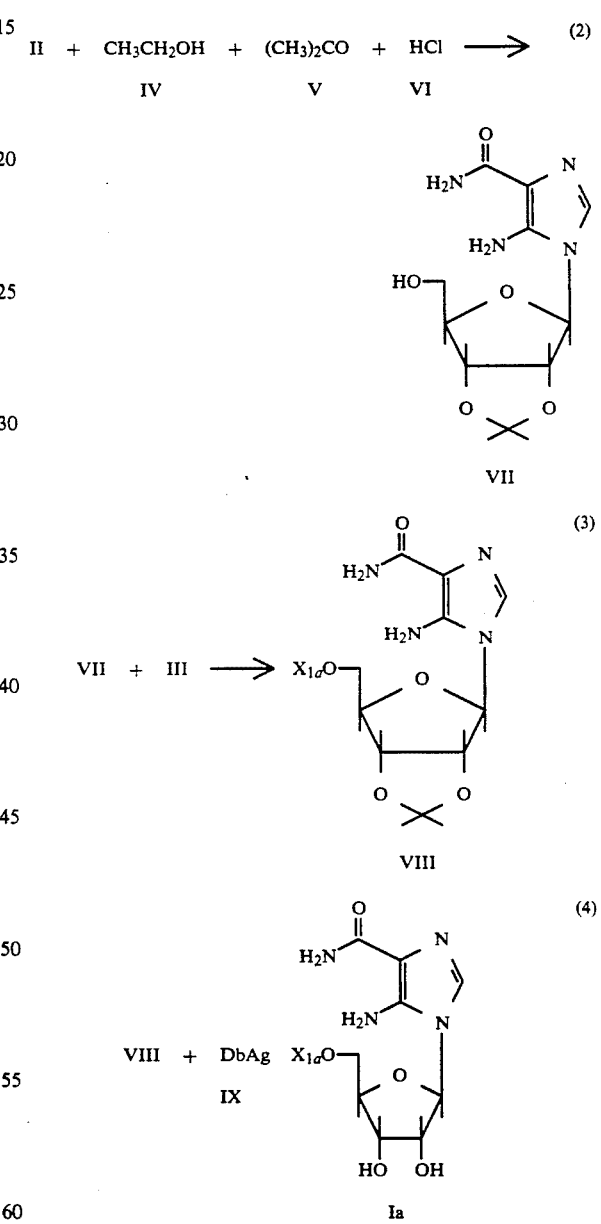

wherein $X_{1a}$

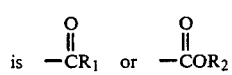

is $-CR_1$ or $-COR_2$ and DbAg is a deblocking agent.

is 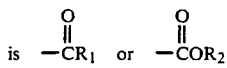

Reaction (2) is conducted by combining II, IV, V and VI. Although the reactants may be combined in any order, it may be preferred to add II to a mixture of IV, V and VI. The reaction is carried out at a temperature of about 10° C. to about 25° C., preferably from about 15° C. to about 25° C. and is generally complete within about 45 minutes. Intermediate VI is isolated by conventional procedures.

Reaction (3) is the reaction of intermediate VII with the appropriate acid chloride, acid anhydride or chloroformate and is carried out as described in connection with Reaction (1).

Reaction (4) is an optional step to remove, if desired, the cyclic blocking group from the 2' and 3' positions. It is carried out by reacting with IX, the appropriate deblocking agent. Suitable deblocking agents include H+resin in water/acetone, tetraethyl-ammonium fluoride/THF, acetic acid/water, formic acid/water and the like. Such deblocking reactions are conventional and well known to those skilled in the art.

Mixed ester compounds may be conveniently prepared by first reacting AICA riboside with the appropriate acid chloride or acid anhydride according to Reaction (1) to add the acyl ester group and then reacting the acyl ester-substituted compound with the appropriate chloroformate according to Reaction (1) to obtain the mixed ester. Alternatively, mixed ester compounds may be prepared by first converting AICA riboside to a monoacyl ester according to Reaction (1), Reaction (2) and then reacting the purified monoacylated product with the appropriate chloroformate according to Reaction (1). In addition, some mixed esters are prepared by first converting AICA riboside to a monoalkoxycarbonate according to Reaction (1) or (2) and then reacting the purified carbonate ester with an appropriate acid chloride or acid anhydride according to Reaction (1).

Utility

The methods of the present invention involve treatment of neurodegenerative disease using agents which enhance extra-cellular adenosine concentrations. As noted, adenosine regulating agents including AICA riboside and the AICA riboside prodrug compounds described herein are useful in treating such conditions where increased extracellular concentrations of adenosine are beneficial.

In the studies described herein, we have used two agents, MPTP and methamphetamine, which induce neurodegenerative and Parkinson's-like conditions in animals. Neurodegeneration was induced in male Swiss-Webster mice by four systemic injections of either 20 mg/kg of MPTP or 5 mg/kg of methamphetamine, two hours between each. CHA was administered in three injections of 0.5 mg/kg at zero, three and six hours relative to the first toxin injection. Ketamine was coadministered with the toxins at 100 mg/kg per injection. Animals were permitted to survive for seven days before sacrifice, upon which the brains were removed and the striata dissected out. The tissue was homogenized and analyzed for tyrosine hydroxylase activity by the method of Reinhard et al. (Life Sciences 39:2185-2189).

Both Meth and MPTP induced a 40-45% reduction in striatal tyrosine hydroxylase activity. Treatment with either CHA ($p<0.01$) or Ketamine (a glutamine receptor antagonist) ($p<0.05$) was effective in completely reversing the Meth induced decrement. Ketamine, while not tried by us, was not reported to be effective by Sonsalla et al. against MPTP. CHA, on the other hand, completely prevented the decrement in this model as well ($p<0.01$). In both models, it was possible to partially reverse the protection afforded by CHA by coadministration of the adenosine antagonist, caffeine (30-50mg/kg).

CHA protected against the development of both MPTP and methamphetamine induced Parkinsonian syndrome. This is a superior protection than that reported for the EAA blockers which have only been shown to be significantly effective by the tyrosine hydroxylase discriminator, in the methamphetamine model. The ineffectiveness of the NMDA-specific EAA receptor blocker MK-801 is shown in FIG. 4. Additionally, the doses of CHA required are not highly sedative unlike those of the EAA blockers. This protection is adenosine receptor mediated since it can be reversed by an adenosine receptor antagonist. This data suggests that adenosine may be an endogenous neuroprotective agent in Parkinson's neurodegeneration, and demonstrates the potential use of adenosinergic strategies for the treatment of Parkinson's disease.

According to one aspect of the present invention, we have found that adenosine receptor agonists can afford significant protection against experimentally induced Parkinson's disease in animals. This disease is one that progresses over a long period (years) and can generally be recognized initially by a mild tremor. Current treatments involve symptom abatement (L-DOPA) but do not block the progression of the disease. According to methods of the present invention, we propose to utilize agents which act via an adenosine mechanism (adenosinergic) to inhibit this progressive deterioration in Parkinson's patients. By "adenosinergic agents" are meant either one or a combination of the following: 1) adenosine receptor agonists; 2) adenosine transport inhibitors; or 3) enzyme inhibitors or activators that raise extracellular adenosine concentrations. One or a combination of the above agents may be administered chronically on probably a daily basis. Due to the chronic, long-term aspect of the treatment it is envisioned that agents of category 2 or 3 will most probably be employed since their actions are more subtle in nature and their side effect profile much more manageable.

The adenosine receptor agonist, cyclohexyladenosine (CHA), has been shown to inhibit the development of the Parkinson's syndrome in rats in both the MPTP and methamphetamine models. Decrease in striatal (an area of the limbic system rich in dopamine which selectively degenerates in Parkinson's Disease) tyrosine hydroxylase in response to either MPTP or methamphetamine was monitored. Administration of CHA was shown to accord significant protection in both the MPTP and methamphetamine models. (See Examples 1 to 4 and FIGS. 1 to 4.)

It is anticipated that adenosinergic compounds useful in the methods of the present invention will be effectively administered in amounts ranging from about 0.01 mg/kg/day to about 500 mg/kg/day, preferably from about 15 mg/kg/day to about 200 mg/kg/day. That range of dosages should be especially suitable for compounds useful in the invention as prophylactics for the prevention of neurodegenerative damage associated with undesired restricted or decreased blood flow. The use of at least about 0.1 mg/kg/day of AICA riboside or AICA ribotide, preferably from about 1.0 mg/kg/day to about 500 mg/kg/day for said prophylaxis and, more preferably, from about 20 mg/kg/day to about 100 mg/kg/day, is further anticipated. For some of the adenosinergic compounds, a dosage of more than 200–500 mg/kg/day may be needed because of the blood/brain barrier. The use of brain-directed prodrugs may, however, enable a lower dosage.

To deliver these adenosinergic compounds to patients, it is anticipated that they will most often be administered orally, since these compounds (such as prodrugs of AICA ribotide) are not readily degraded by extracellular enzymes in the body or by exposure to low pH present in the stomach. These compounds can also be administrated intravenously, by direct intramuscular injection, subcutaneously, topically to skin or mucous membranes, rectally, or by inhalation. Compositions acceptable for pharmaceutical use are well known. Prodrugs may also be utilized, i.e., those which, when introduced into the body, metabolize to the active forms of the adenosinergic agents.

To assist in understanding the present invention, the following examples are described which include the results of a series of experiments. The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

EXAMPLE 1

Striatal decrement was induced in male Swiss Webster mice by four systemic administrations of 5 mg/kg of (+) methamphetamine, two hours between each. CHA was administered in three doses of 1 mg/kg, the first preceding the first methamphetamine injection by 15 minutes, and the others three and six hours following the first. Ketamine was administered in four doses of 100 mg/kg. These injections coincided with the methamphetamine injections, as did the injections of 0.9% saline. All of the compounds were delivered as an intraperitoneal bolus in a saline vehicle at a volume of 1 ml/100g animal body weight.

Seven days later, the animals were sacrificed and the brains quick frozen on dry ice. Brains were later thawed in 50 mM potassium phosphate buffer (pH 6.1) and the striata dissected out. The tissue from the two hemispheres of each brain was combined and homogenized in 100 $\mu$l of the same buffer containing 0.2% triton x-100, and centrifuged for ten minutes at 17,000×g. The supernatant was analyzed for tyrosine hydroxylase activity by the method of J. F. Reinhard, et al. [Life Sci. 39, 2185 (1986)] in 50 mM phosphate buffer (pH 6.1) with 6,7-Dimethyl tetrahydropterin as a cofactor.

Results are shown in FIG. 1.

EXAMPLE 2

Striatal decrement was induced in mice using the same protocol as that described in Example 1. Ketamine was again administered in four injections of 100 mg/kg coincident with the methamphetamine, but in this experiment, the saline injections were at zero, three and six hours after the first methamphetamine injection as were the administrations of the other drugs. CHA was given as three injections of either 1 mg/kg, 0.5 mg/kg, or 0.5 mg/kg plus 30 mg/kg of caffeine.

Seven days later, animals were sacrificed and their striata dissected out. The striata from the two hemispheres of each brain were combined, weighed and homogenized in ten volumes of 50 mM potassium phosphate buffer with 0.2% triton x-100. The homogenates were spun at 17,000×g and the supernatants analyzed for tyrosine hydroxylase activity as described in FIG. 1.

Figure 2:
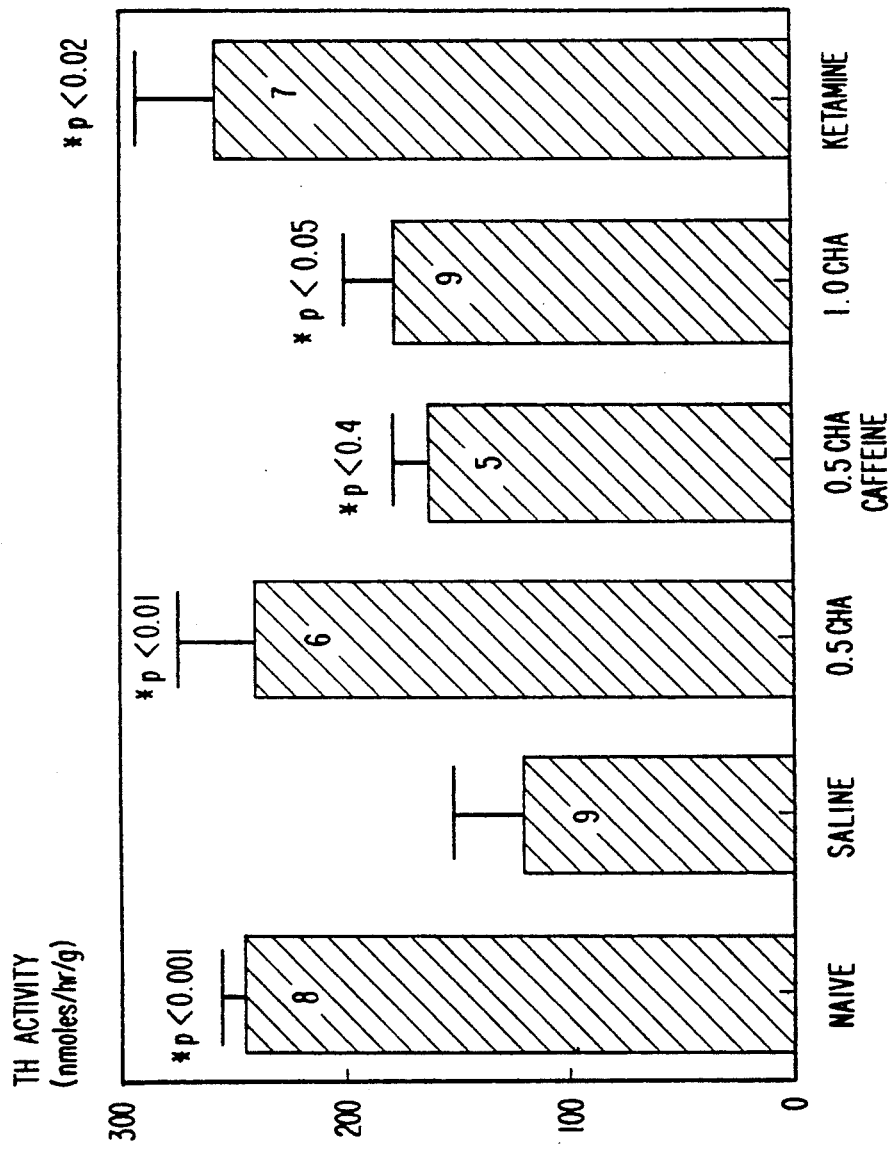
FIG. 2 depicts the effect of Ketamine and CHA (in the presence and absence of caffeine) on methamphetamine-induced Parkinson's Syndrome development.

Results are shown in FIG. 2.

EXAMPLE 3

MPTP was used to induce the Parkinson's syndrome in mice by four systemic administrations of 20 mg/kg with two hours between each. CHA at 0.5 mg/kg/injection or this plus 50 mg/kg/injection of caffeine was administered in three injections, zero, three and six hours from the first MPTP injection as were injections of 0.9% saline. All injections were given as an intraperitoneal bolus injection in a volume of 1 ml/100 g body weight.

Seven days later, animals were sacrificed, and their brains removed. Their striata were dissected out, the two hemispheres combined, weighed and homogenized in one volume of 50 mM potassium phosphate buffer (pH 6.1). These homogenates were then assayed for tyrosine hydroxylase activity as described in connection with Example 1.

Figure 3:
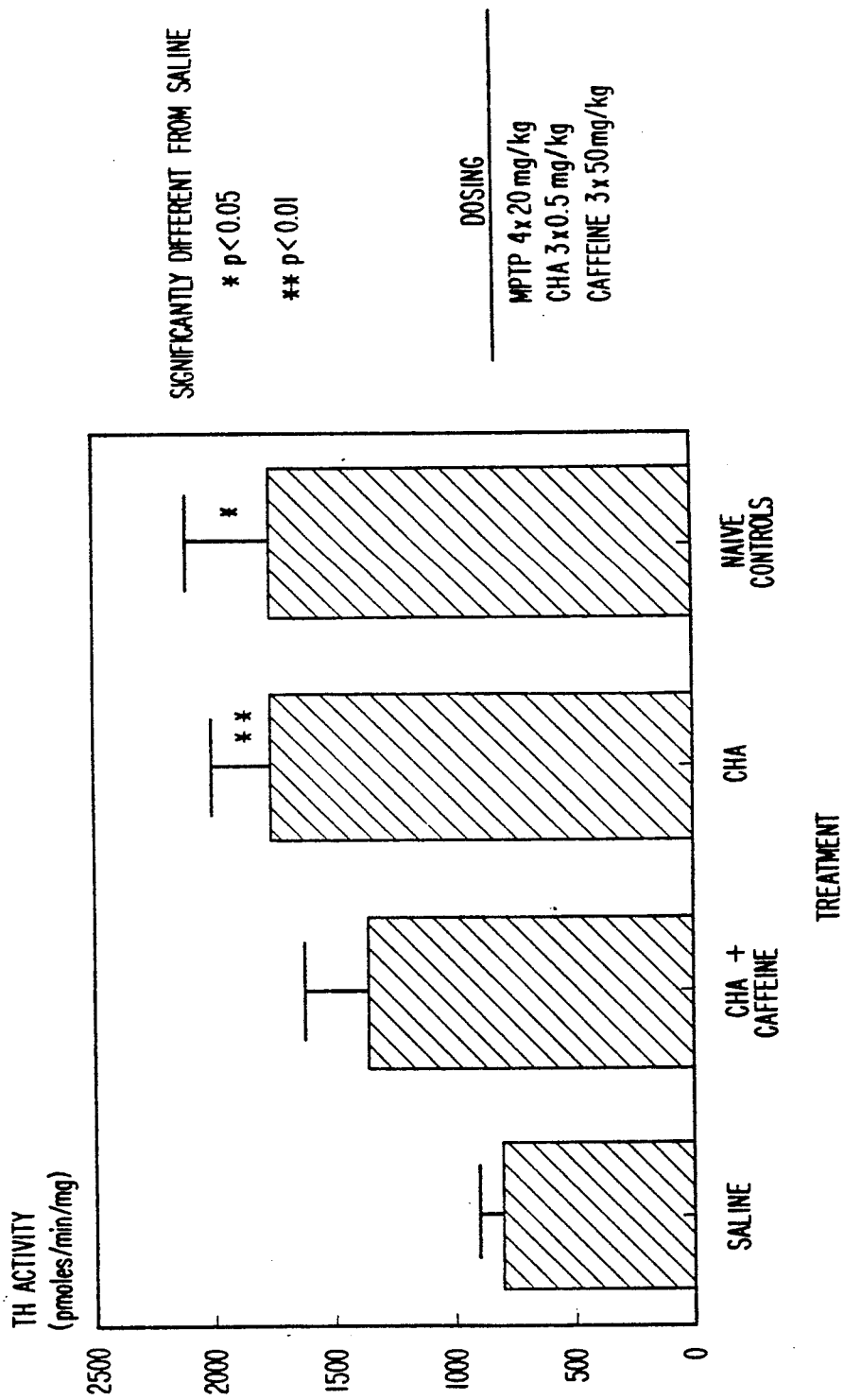
FIG. 3 depicts the effect of CHA on MPTP-induced decreased tyrosine hydroxylase activity.

Results are shown in FIG. 3.

EXAMPLE 4

MPTP was used to induce the Parkinson's syndrome in mice according to the procedure described in Example 3. CHA (0.5 mg/kg) and MK-801 (3.5 mg/kg) were administered in three injections, zero, three and six hours from the first MPTP injection, as were injections of 0.9% saline. All injections were given as an intraperitoneal bolus injection in a volume of 1 ml/100 g body weight.

Strial tyrosine hydroxylane activity was assayed as described in Example 3.

Results are shown in FIG. 4.

We claim:

1. A method of preventing neural tissue damage caused by excitotoxicity due to increased release of excitatory amino acids in an affected animal wherein said excitotoxicity is caused by or causes a neurodegenerative condition which comprises increasing the extracellular concentration of adenosine in and about said neural tissue.

2. A method according to claim 1 wherein said adenosine concentrations are increased by administering to said individual a therapeutically effective amount of an agent which increases the extracellular concentration of adenosine in and about said neural tissue.

3. A method according to claim 2 wherein said agent comprises an adenosine regulating agent, an adenosine agonist, or an adenosine transport inhibitor.

4. A method according to claim 3 wherein said agent comprises an adenosine agonist.

5. A method according to claim 3 wherein said agent comprises an adenosine regulating agent.

6. A method according to claim 2 wherein said neural tissue is brain or spinal chord.

7. A method according to claim 6 wherein said excitotoxicity is caused by or causes brain trauma.

8. A method according to claim 2 wherein said neurodegenerative condition is Parkinson's Disease, Alzheimer's Disease, Amyotrophic Lateral Sclerosis or Huntington's Disease.

9. A method according to claim 8 wherein said agent comprises an adenosine regulating agent, an adenosine agonist, or an adenosine transport inhibitor.

10. A method of decreasing neural tissue damage associated with a neurodegenerative disease in an affected individual which comprises increasing the extracellular concentration of adenosine in said neural tissue.

11. A method according to claim 10 wherein said adenosine concentration are increased by administering to said individual a therapeutically effective amount of an adenosine-concentration increasing agent.

12. A method according to claim 11 wherein said adenosine consentration increasing agent comprises an adenosine regulating agent, an adenosine agonist, or an adenosine transport inhibitor.

13. A method according to claim 12 wherein said adenosine concentration increasing agent comprises an adenosine regulating agent.

14. A method according to claim 13 wherein said adenosine regulating agent comprises a purine nucleoside or analog or prodrug thereof.

15. A method according to claim 14 wherein said adenosine regulating agent comprises AICA riboside or an AICA riboside prodrug or analog.

16. A method according to claim 12 wherein said adenosine concentration increasing agent comprises an adenosine agonist.

17. A method according to claim 12 wherein said neurodegenerative disease is Parkinson's Disease, Alzeheimer's Disease, Amyotropic Lateral Sclerosis or Huntington's Disease.

18. A method of preventing neural tissue damage associated with a neurodegenerative condition which comprises the prophylactic administration of a therapeutically effective amount of an agent which increases the extracellular concentration of adenosine.

19. A method according to claim 18 wherein said neurodegenerative condition comprises Parkinson's disease.

20. A method according to claim 18 wherein said agent comprises an adenosine regulating agent, an adenosine agonist, or an adenosine transport inhibitor.

21. A method according to claim 20 wherein said agent comprises an adenosine agonist.

22. A method according to claim 20 wherein said agent comprises an adenosine regulating agent.

23. A method according to claim 20 wherein said neurodegenerative disease is Parkinson's Disease, Alzheimer's Disease, Amytropic Lateral Sclerosis or Huntington's Disease.

24. A method of decreasing progressive brain deterioration associated with a neurodegenerative disease in an animal afflicted therewith which comprises administering to said animal a therapeutically effective amount of an agent which increases the extracellular concentration of adenosine.

25. A method according to claim 24 wherein said agent is an adenosine regulating agent, an adenosine agonist, or an adenosine transport inhibitor.

26. A method according to claim 25 wherein said neurodegenerative disease is Parkinson's Disease, Alzheimer's Disease, Amyotrophic Lateral Sclerosis, or Huntington's Disease.

* * * * *

UNITED STATES PATENT AND TRADEMARK OFFICE
CERTIFICATE OF CORRECTION

PATENT NO. : 5,187,162
DATED : FEBRUARY 16, 1993
INVENTOR(S) : PAUL MARANGOS, HARRY GRUBER

It is certified that error appears in the above-identified patent and that said Letters Patent is hereby corrected as shown below:

On title page, item [56] insert

PUBLICATIONS: PHILLIS, ET AL. "A POTENT DEPRESSANT ACTION OF ADENINE DERIVATIVES ON CEREBRAL CORTICAL NEURONES" EUROP. J. PHARMACOL 30: [125-129] 125-139 (1975).

COLUMN 4, LINE 26: SEIZURE ACTIVITY. BESIDES

COLUMN 4, LINE 60: OR AICA [RIBO-SIDE] RIBOSIDE

Column 5, LINE 45: [("MPP.")] ("MPP$^{+}$.")

COLUMN 7, LINE 18: [U.S. PAT. NO.] USSN

COLUMN 7, LINE 34: AICA RIBOSIDE ITSELF. THE

Signed and Sealed this

Sixteenth Day of August, 1994

Attest:

BRUCE LEHMAN

*Attesting Officer*    *Commissioner of Patents and Trademarks*